United States Patent
Markle et al.

(10) Patent No.: US 6,602,723 B1
(45) Date of Patent: Aug. 5, 2003

(54) METHOD OF INTEGRATING SCATTEROMETRY METROLOGY STRUCTURES DIRECTLY INTO DIE DESIGN

(75) Inventors: Richard J. Markle, Austin, TX (US); James Broc Stirton, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 24 days.

(21) Appl. No.: 09/824,285

(22) Filed: Apr. 2, 2001

(51) Int. Cl.[7] .............................................. H01L 21/66
(52) U.S. Cl. ............................................ 438/5; 438/16
(58) Field of Search ............................ 438/16, 5, 7, 8, 438/9, 14, 15, 17, 18, 10, 11, 12

(56) References Cited

U.S. PATENT DOCUMENTS

| | | | |
|---|---|---|---|
| 4,898,471 A | * 2/1990 | Vaught et al. ............ | 356/237.4 |
| 5,076,692 A | * 12/1991 | Neukermans et al. ....... | 250/574 |
| 5,867,276 A | 2/1999 | McNeil et al. .............. | 356/445 |
| 5,877,860 A | 3/1999 | Borden ........................ | 356/376 |
| 5,880,838 A | 3/1999 | Marx et al. .................. | 356/351 |
| 6,051,348 A | 4/2000 | Marinaro et al. ............. | 430/30 |
| 6,081,334 A | 6/2000 | Grimbergen et al. ........ | 356/357 |
| 6,245,584 B1 | 6/2001 | Marinaro et al. ............. | 438/14 |

\* cited by examiner

Primary Examiner—Evan Pert
(74) Attorney, Agent, or Firm—Williams, Morgan & Amerson, P.C.

(57) ABSTRACT

The present invention is directed to a method of incorporating metrology grating structures into die design. In one embodiment, the invention is directed to a wafer comprised of a semiconducting substrate, a plurality of production die formed on the substrate, and at least one non-production die formed on the substrate, the non-production die having at least one grating structure formed therein that will ultimately be measured in subsequent metrology tests. The present invention is also directed to a method that comprises providing a semiconducting substrate, forming at least one production integrated circuit device in a plurality of production die formed on the substrate, and forming at least one grating structure in the non-production die. The method further comprises illuminating at least one of the grating structures formed in the non-production die and measuring light reflected off of the illuminated grating structure to generate an optical characteristic trace for the illuminated grating structure formed in the non-production die.

27 Claims, 6 Drawing Sheets

METHOD OF INTEGRATING SCATTEROMETRY METROLOGY STRUCTURES DIRECTLY INTO DIE DESIGN

BACKGROUND OF THE INVENTION

1. Field of the Invention

This invention relates generally to semiconductor fabrication technology, and, more particularly, to a method of integrating scatterometry metrology directly into die design, and a substrate having one or more die that are substantially comprised of grating structures used in scatterometry measurement techniques.

2. Description of the Related Art

There is a constant drive within the semiconductor industry to increase the operating speed of integrated circuit devices, e.g., microprocessors, memory devices, and the like. This drive is fueled by consumer demands for computers and electronic devices that operate at increasingly greater speeds. This demand for increased speed has resulted in a continual reduction in the size of semiconductor devices, e.g., transistors. That is, many components of a typical field effect transistor (FET), e.g., channel length, junction depths, gate insulation thickness, and the like, are reduced. For example, all other things being equal, the smaller the channel length of the transistor, the faster the transistor will operate. Thus, there is a constant drive to reduce the size, or scale, of the components of a typical transistor to increase the overall speed of the transistor, as well as integrated circuit devices incorporating such transistors.

Figure 1:
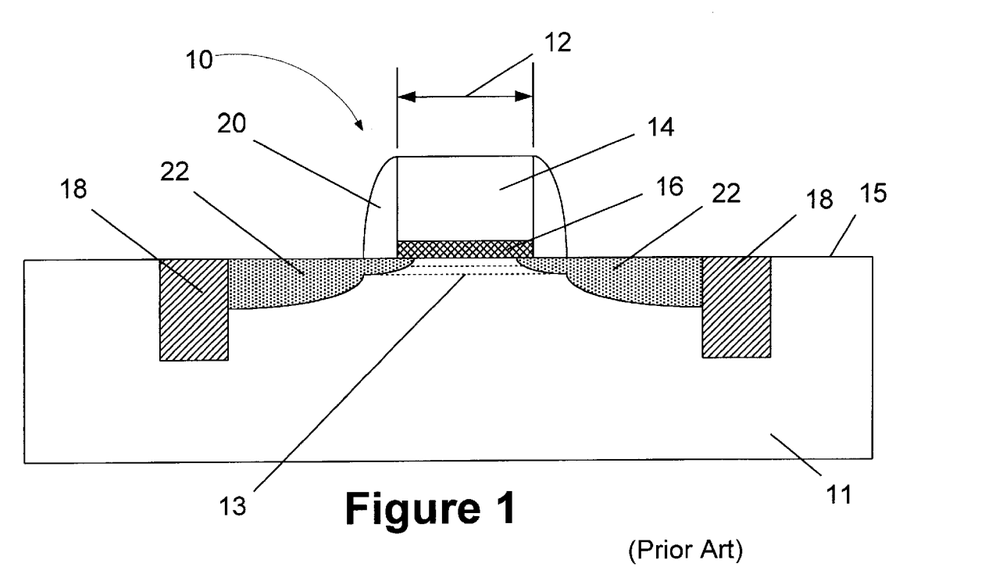
FIG. 1 is a cross-sectional view of an illustrative prior art transistor.

By way of background, an illustrative field effect transistor 10, as shown in FIG. 1, may be formed above a surface 15 of a semiconducting substrate or wafer 11 comprised of doped-silicon. The substrate 11 may be doped with either N-type or P-type dopant materials. The transistor 10 may have a doped polycrystalline silicon (polysilicon) gate electrode 14 formed above a gate insulation layer 16. The gate electrode 14 and the gate insulation layer 16 may be separated from doped source/drain regions 22 of the transistor 10 by a dielectric sidewall spacer 20. The source/drain regions 22 for the transistor 10 may be formed by performing one or more ion implantation processes to introduce dopant atoms, e.g., arsenic or phosphorous for NMOS devices, boron for PMOS devices, into the substrate 11. Shallow trench isolation regions 18 may be provided to isolate the transistor 10 electrically from neighboring semiconductor devices, such as other transistors (not shown). Additionally, although not depicted in FIG. 1, a typical integrated circuit device is comprised of a plurality of conductive interconnections, such as conductive lines and conductive contacts or vias, positioned in multiple layers of insulating material formed above the substrate. These conductive interconnections allow electrical signals to propagate between the transistors formed above the substrate.

The gate electrode 14 has a critical dimension 12, i.e., the width of the gate electrode 14, that approximately corresponds to the channel length 13 of the device when the transistor 10 is operational. Of course, the critical dimension 12 of the gate electrode 14 is but one example of a feature that must be formed very accurately in modern semiconductor manufacturing operations. Other examples include, but are not limited to, conductive lines, openings in insulating layers to allow subsequent formation of a conductive interconnection, i.e., a conductive line or contact, therein, etc.

In general, semiconductor manufacturing operations involve, among other things, the formation of layers of various materials, e.g., polysilicon, insulating materials, etc., and the selective removal of portions of those layers by performing known photolithographic and etching techniques. These processes are continued until such time as the integrated circuit device is complete. During the course of fabricating such integrated circuit devices, a variety of features, e.g., gate electrodes, conductive lines, openings in layers of insulating material, etc., are formed to very precisely controlled dimensions. Such dimensions are sometimes referred to as the critical dimension (CD) of the feature. It is very important in modem semiconductor processing that features be formed as accurately as possible due to the reduced size of those features in such modem devices. For example, gate electrodes may now be patterned to a width 12 that is approximately 0.2 μm (2000 Å), and further reductions are planned in the future. As stated previously, the width 12 of the gate electrode 14 corresponds approximately to the channel length 13 of the transistor 10 when it is operational. Thus, even slight variations in the actual dimension of the feature as fabricated may adversely affect device performance.

Figure 2:
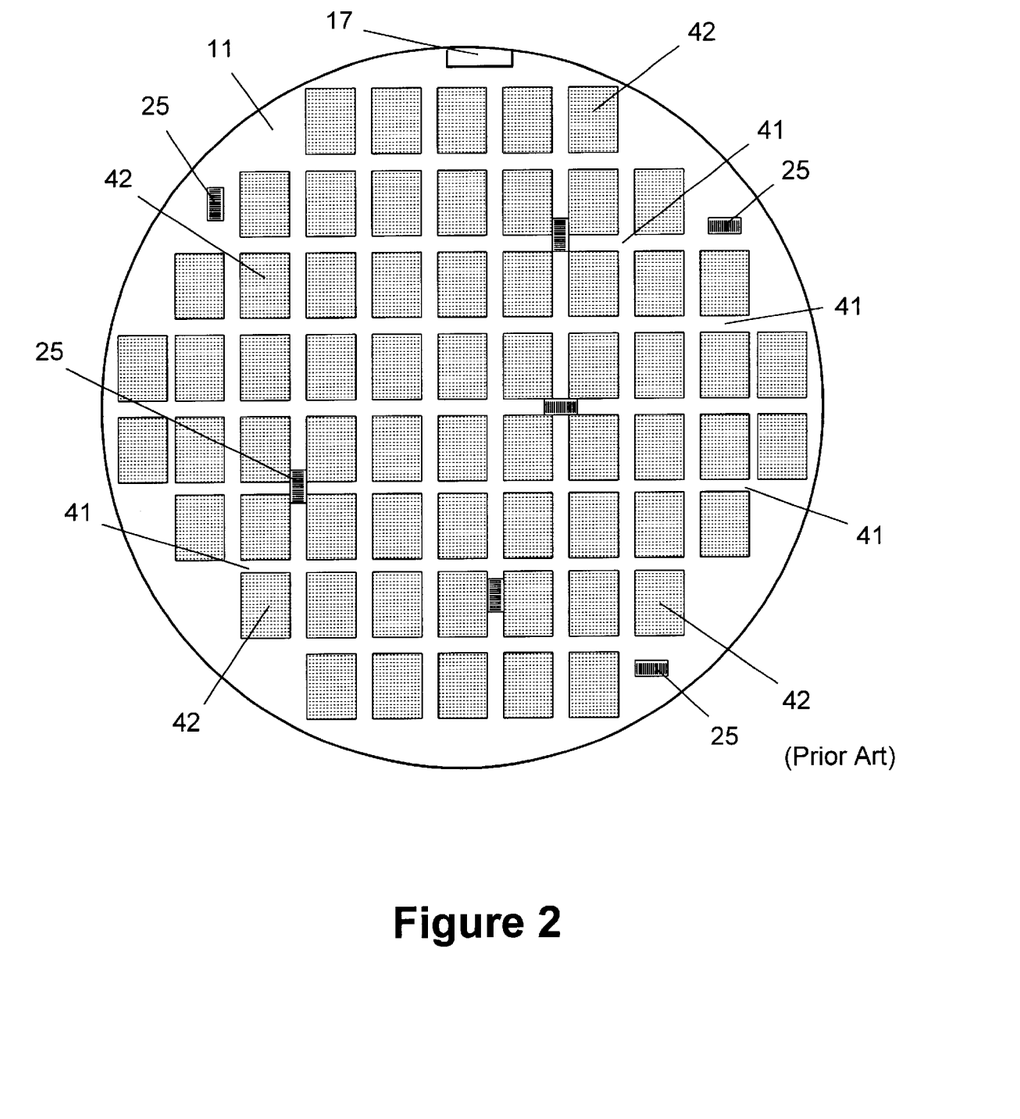
FIG. 2 is a plan view of an illustrative wafer II having a plurality of production die formed thereabove.

In the process of forming integrated circuit devices, millions of transistors, such as the illustrative transistor 10 depicted in FIG. 1, are formed above a semiconducting substrate. FIG. 2 depicts an illustrative embodiment of a semiconducting substrate or wafer 11 that may be found in modem semiconductor manufacturing operations. As shown in FIG. 2, a plurality of production die 42 are formed above the wafer 11. The production die 42 define the area of the wafer 11 where production integrated circuit devices, e.g., microprocessors, ASICs, memory devices, etc., will be formed. The size, shape and number of production die 42 per wafer 11 depend upon the type of device under construction. For example, several hundred production die 42 may be formed above an 8-inch diameter wafer 11. The wafer 11 may also have an alignment notch 17 that is used to provide relatively rough alignment of the wafer 11 prior to performing certain processes, e.g., an exposure process in a stepper tool. The space between the production die 42 is generally referred to as scribe lines 41. After the integrated circuits are completely formed on the production die 42, the wafer 11 will be cut along the scribe lines 41 and packaged and sold. Typically, the production die 42 are packed very close together, i.e., the scribe lines 41 may have a width that ranges from approximately 25–200 μm.

During the course of manufacturing integrated circuit devices, it is highly desirable and important to obtain as much information as possible regarding how well the processes used to form the various features, e.g., gate electrodes, metal lines, trenches, etc., performed. To this end, a variety of metrology tests and tools are used to obtain a variety of data regarding the processes and resulting features formed on an integrated circuit device. For example, an ellipsometer may be used to determine the thickness of a previously formed layer of material, e.g., silicon dioxide. Similarly, a scanning electron microscope may be used to approximately determine the critical dimension of gate electrode structures 14 after they have been formed.

Scatterometry is another metrology technique that has found application within semiconductor manufacturing operations. Typically, scatterometry involves the formation of one or more grating structures 25 that will be subsequently measured using a scatterometry tool. These grating structures 25 may be positioned at various locations on the wafer 11, and they may be oriented in multiple directions. Typically, the grating structures 25 are located in the scribe lines 41 of the wafers 11. Seven illustrative grating structures 25 are depicted in FIG. 2. The size and shape of the grating structures 25 may be varied, but they do tend to be relatively large, e.g., they may be formed in an area having dimensions of approximately 100×120 μm. Given the size of these grating structures 25, there may be some situations where, given current practices, one or more of the grating structures 25 cannot be placed in an ideal location. In turn, this may deny the process engineer valuable metrology data that may be useful in improving manufacturing operations.

Given the scarcity of available plot space, the positioning of the grating structures 25 across the surface of the substrate 11 is often dictated by what plot space is left after the formation of the production die 42. That is, simply put, the placement of the grating structures 25 is given a very low priority compared to the placement of production die 42. This can be problematic in that, all other things being equal, it would be desirable to locate the grating structures 25 used in scatterometric metrology techniques at locations where the most benefit may be derived. For example, all other things being equal, it would be desirable to locate the grating structures 25 at positions on the wafer such that the scatterometry tools may more accurately reflect the processing to which the production integrated circuit devices are subjected. By way of example, it may be desirable to examine the effectiveness of a process used to form gate electrode structures in relation to how densely packed the structures are relative to other surrounding structures. That is, a process used to form an isolated gate electrode structure may produce different results, i.e., critical dimensions, as compared to using the same process in which a plurality of gate electrode structures are formed in a very densely-packed environment. In such situations, it may be desirable to locate a grating structure 25 in a densely-packed environment, but such environments are not available in the scribe lines 41 of the wafer 11.

The present invention is directed to a method and system that may solve, or at least reduce, some or all of the aforementioned problems.

SUMMARY OF THE INVENTION

The present invention is directed to a method of integrating scatterometry metrology structures directly into die design. In one embodiment, the present invention is directed to a wafer comprised of a semiconducting substrate, a plurality of production die formed on the substrate, and at least one non-production die formed on the substrate, the non-production die having at least one grating structure formed therein that will be measured in subsequent metrology tests. The number of such non-production die, as well as the number of grating structures in each non-production die, may vary. Moreover, the size, shape and configuration of the grating structures may vary from die to die, and within a die.

In another illustrative embodiment, the present invention is also directed to a method comprised of providing a semiconducting substrate, forming at least one production integrated circuit device in a plurality of production die formed on the substrate, and forming at least one grating structure in at least one non-production die formed on the substrate. The method further comprises illuminating said grating structure formed in the non-production die and measuring light reflected off of the illuminated grating structure to generate an optical characteristic trace for the illuminated grating structure formed in the non-production die.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Although the various regions and structures of a semiconductor device are depicted in the drawings as having very precise, sharp configurations and profiles, those skilled in the art recognize that, in reality, these regions and structures are not as precise as indicated in the drawings. Additionally, the relative sizes of the various features and doped regions depicted in the drawings may be exaggerated or reduced as compared to the size of those features or regions on fabricated devices. Nevertheless, the attached drawings are included to describe and explain illustrative examples of the present invention.

In general, the present invention is directed to a method of integrating scatterometry metrology structures directly into die design, and a substrate having one or more die that are comprised of a plurality of grating structures used in scatterometry measurement techniques, but no production integrated circuit devices. As will be readily apparent to those skilled in the art upon a complete reading of the present application, the present method is applicable to a variety of technologies, e.g., NMOS, PMOS, CMOS, etc., and it is readily applicable to a variety of devices, including, but not limited to, logic devices, memory devices, etc.

In general, the inventive methods described herein involve the formation of one or more grating structures in one or more die of a wafer. For ease of reference, die containing one or more of such grating structures will be referred to as non-production die. The grating structures 30 described herein may be formed in a die designed to contain only such grating structures 30, in a die that is comprised of such grating structures and additional open spacing, and in a die that was originally designed to be production die, i.e., die where completed integrated circuit devices were to be formed. In the latter case, the die is connected to a non-production die due to the inclusion of one or more grating structures 30 in the die. In short, the grating structures 30 may be formed in what was previously destined to be a die containing production integrated circuit devices. As a result, such die may contain the grating structures 30 as well as additional components of an integrated circuit device, e.g., a transistor, metal lines, trenches, etc. The grating structures 30 may be added to such a die to convert it to a non-production die at any point during the process. The formation of the relatively larger grating structures 30, e.g., on the order of 100 μm×120 μm or less, in the die of the wafer 11 is believed to be counter to existing practices within the semiconductor manufacturing industry. This is because, in semiconductor manufacturing, emphasis is placed upon maximizing the use of the available plot space, i.e., silicon, to form production devices that may be sold.

Figure 3:
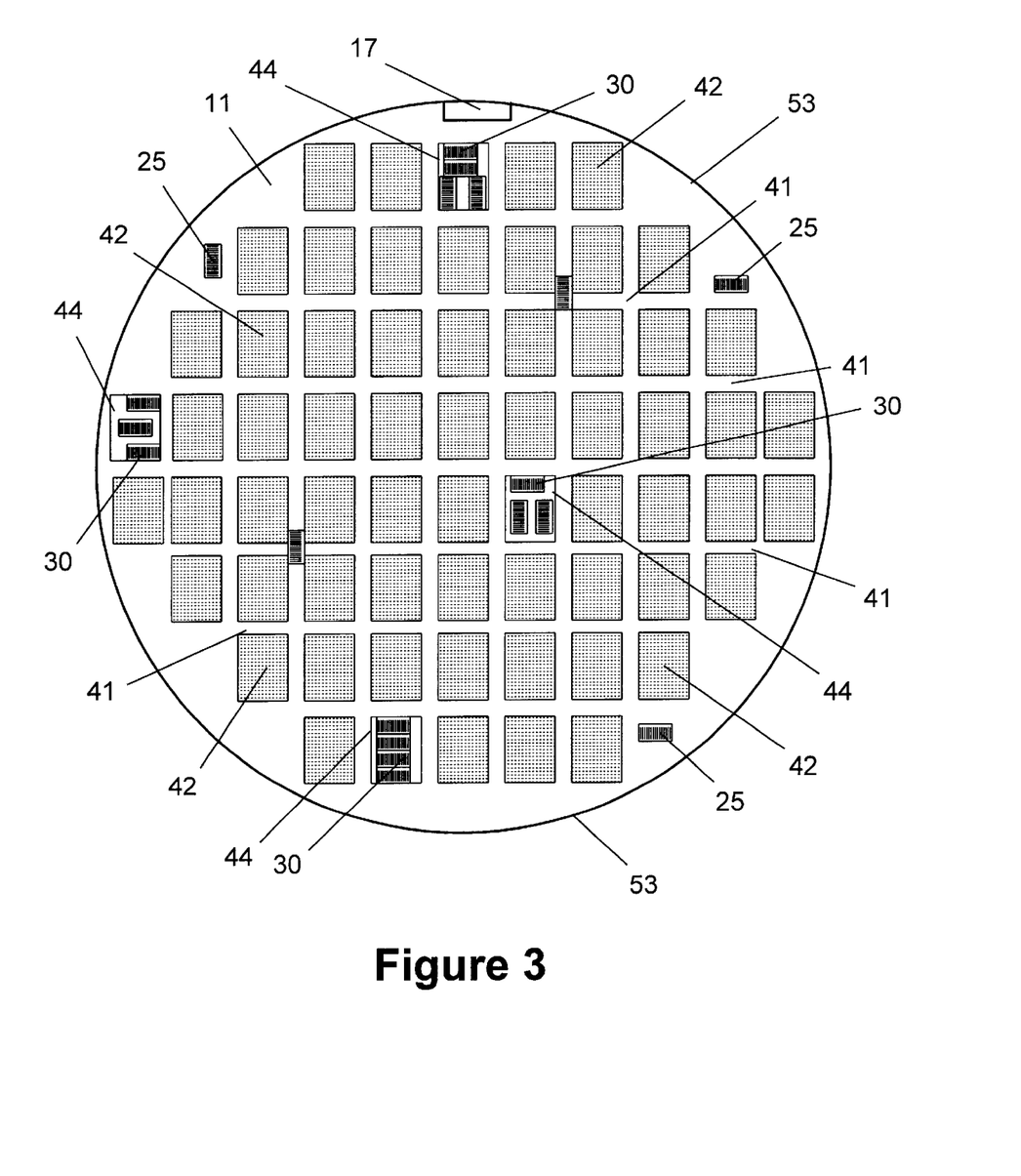
FIG. 3 is a plan view depicting one illustrative embodiment of the present invention.
Figure 4A:
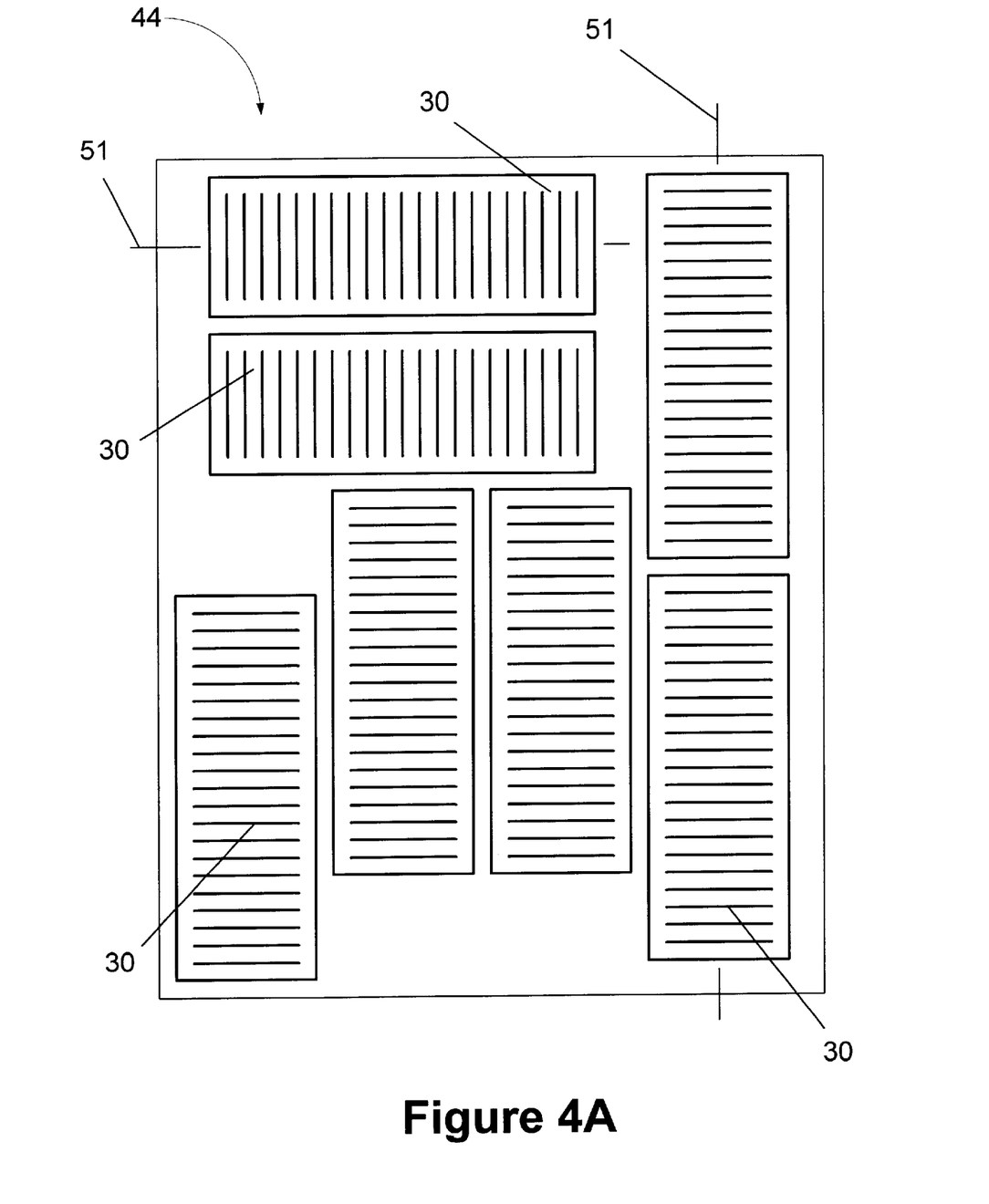
FIG. 4A is a plan view of a die comprised of a plurality of grating structures in accordance with one embodiment of the present invention.

One embodiment of the present invention will now be described with reference to FIGS. 3 and 4A. As shown therein, at least one grating structure 30 is formed in each of a plurality of non-production die 44 formed at various locations across the surface of the wafer 11. That is, in this embodiment the present invention involves providing or creating one or more non-production die 44 on a wafer 11 comprised of at least one grating structure 30 for use in scatterometric metrology techniques. In some embodiments, the non-production die 44 are dedicated in that the die contains grating structures 30 and substantially no additional structure. In other embodiments, at some point during the fabrication process the decision may be made to convert what would otherwise have been a production die 42 into a non-production die 44 by forming a plurality of grating structures on the die. Production integrated circuit devices will be formed in the regular production die 42. Of course, there may be some circuitry or features on the non-production die 44, e.g., leftover features that were formed prior to converting a production die to a non-production die. Other test structures may also be located on the non-production die 44.

A number of grating structures 30 may be formed within each non-production die 44. FIG. 4A depicts an illustrative embodiment wherein seven such grating structures 30 are formed in the illustrative non-production die 44 comprised of the grating structures 30 and open spaces. The illustrative grating structures 30 depicted in FIG. 4A need not be identical in size, shape or configuration. The various grating structures 30 in the non-production die 44 in FIG. 4A may be oriented in a variety of directions. For example, the gratings may be oriented such that the long axis 51 of the grating structure 30 is oriented approximately horizontal, vertical, or at some angle therebetween. Moreover, the various grating structures 30 within a given non-production die 44 may be positioned at different orientations within the non-production die 44, as shown in FIG. 4A. Of course, if desired, all of the grating structures 30 within the non-production die 44 may be oriented in the same direction. Additionally, the orientation of the grating structure 30 within a non-production die 44 may vary from die to die. In one illustrative embodiment, the non-production die 44 may have dimensions of approximately 400–480 μm, and four grating structures 30 (each having a size of approximately 100×120 μm) may be formed therein.

Figure 4B:
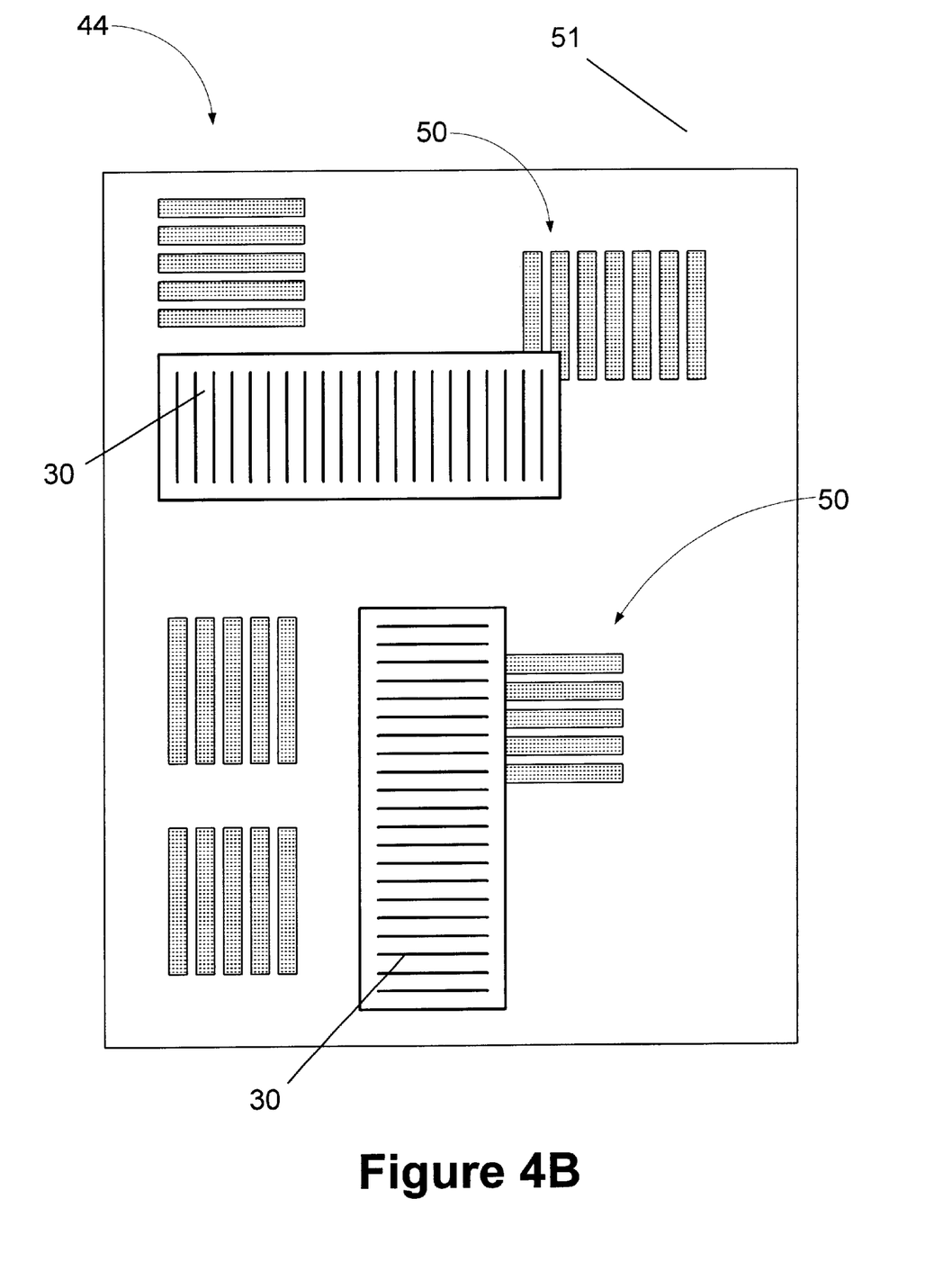
FIG. 4B is a plan view of yet another illustrative embodiment of a die wherein a plurality of grating structures and additional features have been formed within the die.

In other embodiments, the grating structures 30 may be formed in a die that was previously intended to be a production die 42 that contains one or more production integrated circuit devices or features thereof. That is, at some point during the process, e.g., after gate electrode structures are formed, after ion implant processes are performed, or after metal lines are formed, etc., a decision may be made by the appropriate process engineer that a particular die may be converted to a non-production die 44 by the formation of one or more of the grating structures 30 within the die. In such a case, the non-production die 44 may contain a plurality of grating structures 30 and a plurality of features 50 of an integrated circuit device, as shown in FIG. 4B.

The number of non-production die 44 provided on each wafer 11, or within a lot of wafers, may vary depending upon the device under construction and the level of metrology data desired by the appropriate process engineer. Moreover, the spatial relationship between the various non-production die 44 across the surface of the wafer 11 may be varied as a matter of design choice. For example, in the embodiment depicted in FIG. 3, one of the four non-production die 44 is located at the approximate middle of the wafer 11, and the other three non-production die 44 are positioned toward the edge 53 of the wafer 11. A variety of patterns of the non-production die 44 may be used. Moreover, the location of the non-production die 44 may be varied from wafer-to-wafer or from lot-to-lot as a matter of design choice. That is, the non-production die 44 need not be positioned at the same location from wafer-to-wafer. Of course, if desired, the additional grating structures 25 may also be formed at various locations across the surface of the wafer, as indicated in FIG. 3. These additional grating structures 25 may be used in providing additional metrology data to the process engineer.

Figure 5A:
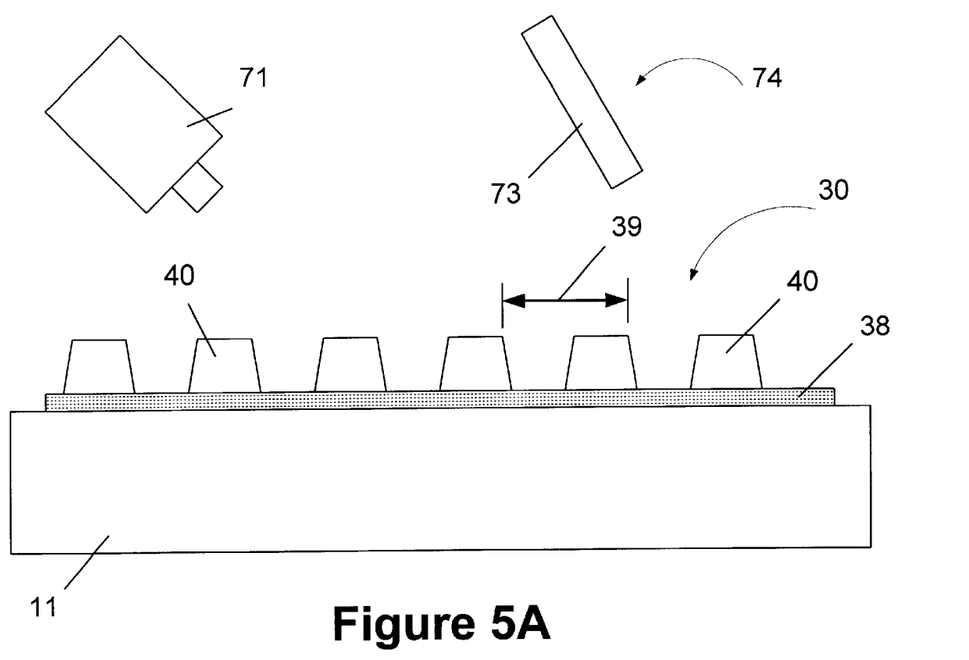
FIGS. 5A–B depict an illustrative grating structure that may be used with the present invention.
Figure 5B:
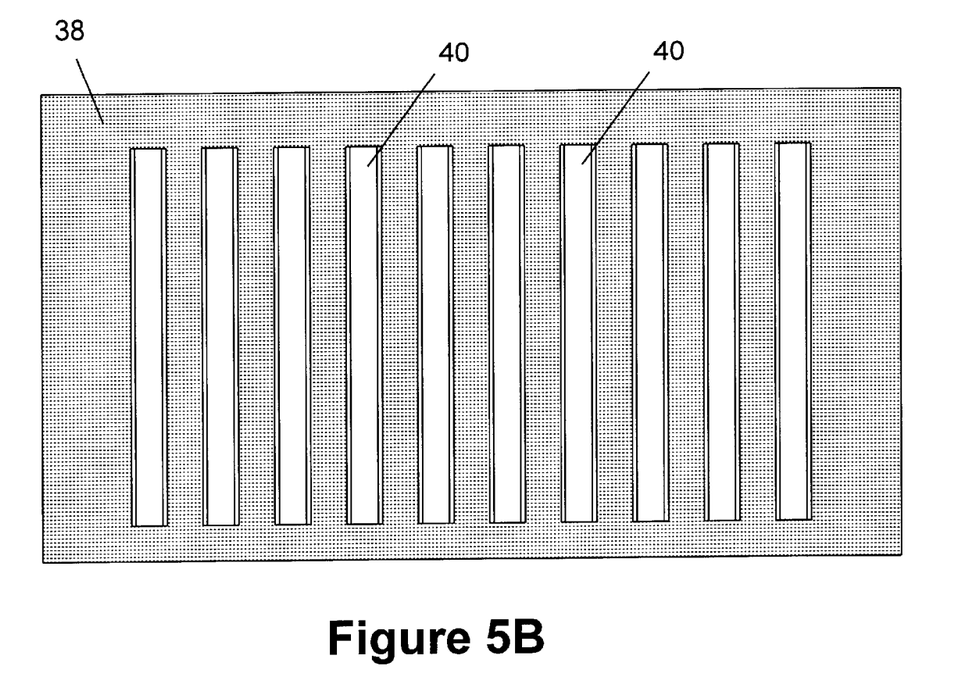

The grating structures 30 may be comprised of a variety of repeating structures, e.g., a plurality of lines or trenches. In one illustrative embodiment, as shown in FIGS. 5A–5B, the grating structures 30 may be comprised of a plurality of gate electrode structures 40 formed above a layer of gate insulation material 38. The gate electrode structures 40 comprising the grating structure 30 may have a pitch 39 that varies from approximately 100–1000 μm. The size, shape and configuration of the grating structure 30 may be varied as a matter of design choice. For example, the grating structure 30 may be formed in an area having approximate dimensions of 100 μm×120 μm, and it may be comprised of approximately 10–12 gate electrode structures 40 (depending upon the selected pitch).

To form the non-production die 44, a separate stepper exposure process may be used. For example, a first stepper exposure process may be performed on all of the production die 42 using a first reticle. Thereafter, a second exposure process may be performed wherein a second reticle is used to expose the non-production die 44, i.e., to begin the process of forming the grating structures 30. Alternatively, the wafer 11 may be subjected to an exposure process in which multiple die are exposed in a single flash, e.g., a 2×2 exposure process (four die), a 5×5 exposure process (25 die). Typically, all of the die exposed during such a multiple die exposure process are production die 42. However, one technique for forming the non-production die 44 of the present invention would involve having a multiple die reticle, wherein the reticle is comprised of patterned lines for both the production die 42 and one or more of the non-production die 44. This latter reticle may then be used to expose areas of the wafer 11 where a non-production die 44 is desired, e.g., in the middle region of the wafer 11 and at one or more locations near the edge 53 of the wafer 11.

A variety of scatterometry tools 74 may be used with the present invention, e.g., so-called 2θ-type systems and lens-type scatterometry tools, to illuminate and measure one or more of the grating structures 30. As shown in FIG. 5A, the scatterometry tool 74 is comprised of an illustrative light source 71 and a collector 73. The scatterometry tool 74 may use white light, or some other wavelength or combination of wavelengths, depending on the specific implementation. Typically, the scatterometry tool 74 will generate an incident beam that has a wide spectral composition and wherein the intensity of the light changes slowly in comparison to changes in wavelength. The angle of incidence of the light may also vary, depending on the specific implementation. The profile traces generated by the scatterometry tool 74 may be based upon a comparison of light intensity to wavelength (for white light, fixed angle type scatterometry tools) or a comparison of intensity to incident angle (for angle resolved systems that use a single light source).

The present invention is directed to a method of integrating scatterometry metrology structures directly into die design. In one embodiment, the present invention is directed to a wafer 11 comprised of a semiconducting substrate, a plurality of production die 42 formed on the substrate 11, and at least one non-production die 44 formed on the substrate 11, the non-production die 44 having at least one grating structure 30 formed therein that will be measured in subsequent metrology tests. The number of such non-production die 44, as well as the number of grating structures 30 in each non-production die 44, may vary. Moreover, the size, shape and configuration of the grating structures 30 may vary from die to die, and within a die 44.

In another illustrative embodiment, the present invention is directed to a method comprising providing a semiconducting substrate, forming at least one production integrated circuit device in a plurality of production die 42 formed on the substrate 11, and forming at least one grating structure 30 in at least one non-production die 44 formed on the substrate 11. The method further comprises illuminating the grating structure 30 formed in the non-production die 44 and measuring light reflected off of the illuminated grating structure 30 to generate an optical characteristic trace for the illuminated grating structure 30 formed in the non-production die 44.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method, comprising:
   providing a semiconducting substrate;
   forming at least one production integrated circuit device in each of a plurality of production die formed on said substrate;
   converting at least one of said plurality of production die to a non-production die by forming at least one grating structure in said at least one production die;
   illuminating said at least one grating structure formed in said non-production die; and
   measuring light reflected off of said illuminated grating structure to generate an optical characteristic trace for said illuminated grating structure formed in said non-productive die.

2. The method of claim 1, wherein providing a semiconducting substrate comprises providing a semiconducting substrate comprised of polysilicon.

3. The method of claim 1, wherein forming at least one production integrated circuit device in each of a plurality of production die formed on said substrate comprises forming at least one production integrated circuit device in each of a plurality of production die formed on said substrate, said production integrated circuit device comprised of at least one of a microprocessor, an application specific integrated circuit, and a memory device.

4. The method of claim 1, wherein forming at least one grating structure in at least one non-production die comprises forming a plurality of grating structures in at least one non-production die.

5. The method of claim 1, wherein forming at least one grating structure in at least one non-production die formed on said substrate comprises forming at least three grating structures in at least one non-production die formed on said substrate.

6. The method of claim 1, wherein forming at least one grating structure in at least one non-production die formed on said substrate comprises forming a plurality of grating structures in each of a plurality of non-production die formed on said substrate.

7. The method of claim 1, wherein illuminating said at least one grating structure formed in said non-production die comprises illuminating said at least one grating structure formed in said non-production die using a scatterometry tool.

8. The method of claim 1, wherein forming at least one grating structure in at least one non-production die formed on said substrate comprises forming a plurality of grating structures of differing sizes in at least one non-production die formed on said substrate.

9. The method of claim 1, wherein forming at least one grating structure in at least one non-production die formed on said substrate comprises forming a plurality of grating structures of the same approximate size in at least one non-production die formed on said substrate.

10. The method of claim 1, wherein forming a plurality of grating structures in at least one non-production die formed on said substrate comprises forming a plurality of grating structures in at least one non-production die formed on said substrate, said grating structures being comprised of a plurality of lines.

11. The method of claim 1, wherein forming at least one grating structure in at least one non-production die formed on said substrate comprises forming a plurality of grating structures in at least one non-production die formed on said substrate, said grating structures being comprised of a plurality of trenches.

12. The method of claim 1, wherein forming at least one grating structure in at least one non-production die formed on said substrate comprises forming a plurality of grating structures in at least one non-production die formed on said substrate, at least some of said grating structures being oriented in different directions.

13. The method of claim 1, wherein forming at least one grating structure in at least one non-production die formed on said substrate comprises forming a plurality of grating structures in at least one non-production die formed on said substrate, at least some of said grating structures being oriented in the same direction.

14. The method of claim 1, further comprising forming an additional grating structure in at least one of a plurality of scribe lines of said wafer.

15. The method of claim 14, further comprising illuminating and measuring light reflected off of said additional grating structure.

16. A method, comprising:
providing a semiconducting substrate comprised of polysilicon;
forming at least one production integrated circuit device in each of a plurality of production die formed on said substrate;
converting a first group of the plurality of production die to a plurality of non-production die by forming a plurality of grating structures in each of the plurality of production die in said first group;
illuminating at least one of said plurality of grating structures formed in said non-production die; and
measuring light reflected off of said illuminated grating structure to generate an optical characteristic trace for said illuminated grating structure formed in said non-productive die.

17. The method of claim 16, wherein forming at least one production integrated circuit device in a plurality of production die formed on said substrate comprises forming at least one production integrated circuit device in a plurality of production die formed on said substrate, said production integrated circuit device comprised of at least one of a microprocessor, an application specific integrated circuit, and a memory device.

18. The method of claim 16, wherein forming a plurality of grating structures in each of a plurality of non-production die formed on said substrate comprises forming at least three grating structures in each of a plurality of non-production die formed on said substrate.

19. The method of claim 16, wherein illuminating at least one of said plurality of grating structures formed in said non-production die comprises illuminating at least one of said plurality of grating structures formed in said non-production die using a scatterometry tool.

20. The method of claim 16, wherein forming a plurality of grating structures in each of a plurality of non-production die formed on said substrate comprises forming a plurality of grating structures of differing sizes in each of a plurality of non-production die formed on said substrate.

21. The method of claim 16, wherein forming a plurality of grating structures in each of a plurality of one non-production die formed on said substrate comprises forming a plurality of grating structures of the same approximate size in each of a plurality of non-production die formed on said substrate.

22. The method of claim 16, wherein forming a plurality of grating structures in each of a plurality of non-production die formed on said substrate comprises forming a plurality of grating structures in each of a plurality of non-production die formed on said substrate, said grating structures being comprised of a plurality of lines.

23. The method of claim 16, wherein forming a plurality of grating structures in each of a plurality of non-production die formed on said substrate comprises forming a plurality of grating structures in each of a plurality of non-production die formed on said substrate, said grating structures being comprised of a plurality of trenches.

24. The method of claim 16, wherein forming a plurality of grating structures in each of a plurality of non-production die formed on said substrate comprises forming a plurality of grating structures in each of a plurality of non-production die formed on said substrate, at least some of said grating structures being oriented in different directions.

25. The method of claim 16, wherein forming a plurality of grating structures in each of a plurality of non-production die formed on said substrate comprises forming, a plurality of grating structures in each of a plurality of non-production die formed on said substrate, at least some of said grating structures being oriented in the same direction.

26. The method of claim 16, further comprising forming an additional grating structure in at least one of a plurality of scribe lines of said wafer.

27. The method of claim 26, further comprising illuminating and measuring light reflected off of said additional grating structure.

* * * * *

UNITED STATES PATENT AND TRADEMARK OFFICE
CERTIFICATE OF CORRECTION

PATENT NO. : 6,602,723 B1
DATED : August 5, 2003
INVENTOR(S) : Richard J. Markle and James Broc Stirton

It is certified that error appears in the above-identified patent and that said Letters Patent is hereby corrected as shown below:

Column 8,
Lines 18-19, "non-productive die" should be -- non-production die --.

Column 9,
Lines 38-39, "non-productive die" should be -- non-production die --.

Signed and Sealed this

Fourteenth Day of October, 2003

JAMES E. ROGAN
*Director of the United States Patent and Trademark Office*